US007803354B2

(12) United States Patent
Biatry

(10) Patent No.: US 7,803,354 B2
(45) Date of Patent: Sep. 28, 2010

(54) COSMETIC AND/OR DERMATOLOGICAL USE OF A COMPOSITION COMPRISING AT LEAST ONE OXIDATION-SENSITIVE HYDROPHILIC ACTIVE PRINCIPLE STABILIZED BY AT LEAST ONE MALEIC ANHYDRIDE COPOLYMER

(75) Inventor: Bruno Biatry, Vincennes (FR)

(73) Assignee: L'oreal, Paris (FR)

( * ) Notice: Subject to any disclaimer, the term of this patent is extended or adjusted under 35 U.S.C. 154(b) by 1279 days.

(21) Appl. No.: 10/424,907

(22) Filed: Apr. 29, 2003

(65) Prior Publication Data

US 2004/0001792 A1 Jan. 1, 2004

Related U.S. Application Data

(60) Provisional application No. 60/394,255, filed on Jul. 9, 2002.

(30) Foreign Application Priority Data

Jun. 20, 2002 (FR) .................................. 02 07638

(51) Int. Cl.
*A61Q 5/08* (2006.01)
*A61Q 5/00* (2006.01)
*A61Q 19/00* (2006.01)
*A61Q 19/02* (2006.01)

(52) U.S. Cl. ...................................................... 424/62
(58) Field of Classification Search ....................... None
See application file for complete search history.

(56) References Cited

U.S. PATENT DOCUMENTS

| | | | |
|---|---|---|---|
| 3,242,051 A | 3/1966 | Hiestand et al. | |
| 3,531,427 A | 9/1970 | Kervenski et al. | |
| 3,714,065 A | 1/1973 | Kitajima et al. | |
| 4,229,430 A | 10/1980 | Fahim et al. | |
| 4,465,629 A | 8/1984 | Maughan | |
| 5,032,384 A | 7/1991 | Yeh et al. | |
| 5,081,111 A | 1/1992 | Akimoto et al. | |
| 5,607,692 A | 3/1997 | Ribier et al. | |
| 5,667,791 A | 9/1997 | Hersh et al. | |
| 5,703,041 A | 12/1997 | Afriat et al. | |
| 5,801,192 A | 9/1998 | Dumas et al. | |
| 5,882,658 A * | 3/1999 | Simon et al. | 424/401 |
| 5,891,452 A | 4/1999 | Sebillote-Arnaud et al. | |
| 5,945,032 A | 8/1999 | Breitenbach et al. | |
| 6,008,274 A | 12/1999 | Meyer et al. | |
| 6,024,942 A | 2/2000 | Tanner et al. | |
| 6,068,847 A | 5/2000 | Aleles et al. | |
| 6,103,267 A | 8/2000 | Mitchnick et al. | |
| 6,126,926 A | 10/2000 | Tanaka et al. | |
| 6,162,448 A | 12/2000 | Nguyen et al. | |
| 6,191,188 B1 | 2/2001 | Hossel et al. | |
| 6,232,373 B1 | 5/2001 | Lappas et al. | |
| 6,531,160 B2 * | 3/2003 | Biatry et al. | 424/490 |
| 6,533,823 B2 | 3/2003 | Nakashimada et al. | |
| 6,596,695 B2 | 7/2003 | Castiel et al. | |
| 6,684,530 B2 | 2/2004 | Opazo | |
| 6,764,693 B1 | 7/2004 | Smith | |
| 2002/0022038 A1 | 2/2002 | Biatry et al. | |
| 2003/0190335 A1 | 10/2003 | Boussouira et al. | |
| 2004/0001792 A1 | 1/2004 | Biatry | |
| 2004/0042990 A1 | 3/2004 | Biatry | |
| 2004/0047824 A1 | 3/2004 | Biatry | |
| 2004/0175342 A1 | 9/2004 | Biatry | |
| 2006/0051424 A1 * | 3/2006 | Kvitnitsky et al. | 424/490 |

FOREIGN PATENT DOCUMENTS

| | | |
|---|---|---|
| DE | 42 28 043 | 3/1994 |
| EP | 0 282 951 | 9/1988 |
| EP | 287 731 | 10/1988 |
| EP | 0 380 367 | 8/1990 |
| EP | 0 815 847 | 1/1998 |
| EP | 0 884 047 | 12/1998 |
| EP | 1 064 924 | 1/2001 |
| EP | 1 133 974 | 9/2001 |
| EP | 1 151 741 | 11/2001 |
| EP | 1 374 849 | 1/2004 |
| EP | 1 374 850 | 1/2004 |
| EP | 1 374 851 | 1/2004 |

(Continued)

OTHER PUBLICATIONS

Franchi, Jocelyne et al. Depigmenting Effects of Calcium D-Pantetheine S-Sulfonate on Human Melanocytes, Jun. 2000, Pigment Cell Research, vol. 13, p. 165.*
Franchi, Jocelynne et al. Depigmenting Effects of Calcium D-Pantetheine S-Sulfonate on Human Melanocytes, Jun. 2000, Pigment Cell Research, vol. 13, p. 165.*
Zreik, et al., Molecular Human Reproduction 1999, 5(4), 299-302.

*Primary Examiner*—Robert A Wax
*Assistant Examiner*—Melissa S Mercier
(74) *Attorney, Agent, or Firm*—Oblon, Spivak, McClelland, Maier & Neustadt, L.L.P.

(57) ABSTRACT

A method for depigmenting and/or lightening the skin and/or hair, including body hair, including applying a composition including at least one oxidation-sensitive hydrophilic active principle chosen from ascorbic acid and its derivatives and at least one maleic anhydride copolymer, comprising one or more maleic anhydride comonomers and one or more comonomers chosen from vinyl acetate, vinyl alcohol, vinylpyrrolidone, olefins comprising from 2 to 20 carbon atoms, and styrene, in a physiologically acceptable medium comprising an aqueous phase, to the skin and/or hair.

19 Claims, No Drawings

FOREIGN PATENT DOCUMENTS

| | | |
|---|---|---|
| EP | 1 374 852 | 1/2004 |
| EP | 1 374 853 | 1/2004 |
| FR | 1 151 741 | 6/1956 |
| FR | 2 737 116 | 1/1997 |
| FR | 2 801 788 | 6/2001 |
| FR | 2 816 316 | 5/2002 |
| JP | 63-226358 | 9/1988 |
| JP | 64-85907 | 3/1989 |
| JP | 03-109308 | 5/1991 |
| JP | 3-109308 | 5/1991 |
| JP | 05-229927 | 9/1993 |
| JP | 09-040543 | 2/1997 |
| JP | 2001-261533 | 9/2001 |
| JP | 2001-354551 | 12/2001 |
| JP | 2002-060315 | 2/2002 |
| JP | 2004-026826 | 1/2004 |
| JP | 2004-035548 | 2/2004 |
| JP | 2004-067676 | 3/2004 |
| JP | 2004-067677 | 3/2004 |
| WO | WO 93/22374 | 11/1993 |
| WO | WO 00/30594 | 6/2000 |
| WO | WO 02/14876 | 2/2002 |
| WO | WO 02/028483 | * 10/2002 |

* cited by examiner

COSMETIC AND/OR DERMATOLOGICAL USE OF A COMPOSITION COMPRISING AT LEAST ONE OXIDATION-SENSITIVE HYDROPHILIC ACTIVE PRINCIPLE STABILIZED BY AT LEAST ONE MALEIC ANHYDRIDE COPOLYMER

REFERENCE TO PRIOR APPLICATIONS

This application claims priority to U.S. provisional application 60/394,255, filed Jul. 9, 2002, and to French patent application 0207638 filed Jun. 20, 2002, both of which are incorporated herein by reference.

The present invention relates to the cosmetic and/or dermatological use of a composition comprising at least one oxidation-sensitive hydrophilic active principle and at least one maleic anhydride copolymer in a physiologically acceptable medium comprising an aqueous phase.

It is known to introduce, into cosmetic compositions, various active principles intended to contribute specific treatments to the skin and/or hair. However, some of these active principles exhibit the disadvantage of being unstable in an aqueous medium and of easily decomposing on contact with water, in particular because of oxidation phenomena. They thus rapidly lose their activity over time and this instability conflicts with the desired effectiveness.

Attempts have thus been made for a long time to formulate ascorbic acid or vitamin C because of its numerous beneficial properties. In particular, ascorbic acid stimulates the synthesis of the connective tissue and in particular of collagen, strengthens the defences of the cutaneous tissue against external attacks, such as ultraviolet radiation and pollution, compensates for vitamin E deficiency of the skin, depigments the skin and has a role in combatting free radicals. These last two properties make it an excellent candidate as cosmetic or dermatological active principle for combatting ageing of the skin or for preventing ageing of the skin. Unfortunately, because of its chemical structure (of α-ketolactone), ascorbic acid is highly sensitive to certain environmental parameters and in particular to oxidation phenomena. There thus ensues rapid decomposition of formulated ascorbic acid in the presence of these parameters and in particular in the presence of oxygen, light or metal ions, as a function of the temperature or under certain pH conditions (Pharm. Acta. Helv., 1969, 44, 611-667; STP Pharma, 1985, 4, 281-286).

Several solutions have thus been envisaged in the prior art for reducing and/or slowing down the decomposition of ascorbic acid.

Provision has thus been made to use ascorbic acid in the form of a chemical derivative (magnesium ascorbyl phosphate or esters of fatty acids and ascorbic acid), but the bioavailability of these derivatives is very low (J. Am. Acad. Dermatol., 1996, 34, 29-33).

The instability of ascorbic acid with respect to oxygen can be improved by using specific packagings, such as twin compartments under an inert atmosphere, as disclosed in U.S. Pat. No. 5,935,584, or alternatively by the use of two-phase emulsions, one phase of which is composed of a dry powder comprising ascorbic acid and the second phase of which is a liquid phase. The mixing of the two phases has to be carried out at the time of use (WO 98/43598). These solutions have disadvantages with regard to the cost and the complexity of the manufacturing operations and significant restrictions with regard to use.

Another solution provided in the prior art consists in using a high concentration of glycols or polyols in order to reduce the solubility of oxygen in the formulation, thus protecting the ascorbic acid (WO 96/24325, EP 0 755 674, U.S. Pat. No. 5,981,578). The polyols can optionally be incorporated in liposomes, as disclosed in U.S. Pat. No. 6,020,367. However, these solutions exhibit the disadvantage of resulting in sticky formulations, the cosmetic quality of which is difficult to improve. Furthermore, the presence of a high concentration of these compounds can lead to phenomena of irritation.

Ascorbic acid can also be formulated in anhydrous media, such as silicones (U.S. Pat. No. 6,194,452), which are capable of creating an anhydrous barrier around ascorbic acid. A major disadvantage of such solutions results from the lack of freshness on application.

The need thus remains for a composition employable in particular in the cosmetics field, in which a hydrophilic active principle which is unstable in an oxidizing medium is stabilized, which is comfortable on application, which does not lead to any skin irritation after application and which is compatible with the constraints of an industrial implementation of its manufacturing process.

The activity of ascorbic acid or of its derivatives on pigmentation has been known for many years. Various mechanisms have been described to explain their effect on the reduction of melanogenesis. The inhibiting effect on tyrosinase has been demonstrated for ascorbic acid (J. Soc. Cosmet. Chem., 42, 1991, p. 361-368). Some of its esters have been used for some years in depigmenting treatments, that is to say, magnesium ascorbyl phosphate and ascorbyl glucoside. More recently, a study has shown that magnesium ascorbyl phosphate can reduce the dendricity of melanocytes (Pigment. Cell. Res., 13, 2000, p. 89-98 and p. 190-192).

The aim of the present invention is to provide a composition comprising an oxidation-sensitive active principle chosen from ascorbic acid and its derivatives, which exhibits good cosmetic properties, both with regard to touch and with regard to tolerance, the preservation of which over time does not require specific precautions, and which retains the depigmenting and/or lightening ability of the active principle.

The Applicant Company has discovered, fortuitously, that the use of maleic anhydride copolymers in compositions in which the aqueous phase includes an oxidation-sensitive active principle, such as ascorbic acid, makes it possible to achieve the abovementioned aim.

To the knowledge of the Applicant Company, such polymers comprising maleic anhydride units have never been used in combination with hydrophilic active principles sensitive to decomposition by oxidation for the purpose of improving their stability. This is true in particular in the case of ascorbic acid.

A subject-matter of the present invention is therefore the cosmetic and/or dermatological use of a composition for depigmenting and/or lightening the skin and/or hair, including body hair, the said composition comprising at least one oxidation-sensitive hydrophilic active principle chosen from ascorbic acid and its derivatives and at least one maleic anhydride copolymer in a physiologically acceptable medium comprising an aqueous phase. The copolymer is present in an amount sufficient to stabilize the said oxidation-sensitive hydrophilic active principle. Preferably, the oxidation-sensitive active principle and the copolymer are both in the aqueous phase.

The use of such a composition furthermore exhibits the advantage of acting both by inhibiting tyrosinase, thus reducing melanogenesis, and also by inhibiting the dendricity of the melanocytes. The depigmenting effect thus obtained is much greater than that obtained, for example, with ascorbic acid alone, which acts solely on melanogenesis.

Another subject-matter of the present invention is the use of a combination composed of at least one oxidation-sensitive hydrophilic active principle chosen from ascorbic acid and its derivatives and of at least one maleic anhydride copolymer in a cosmetic composition comprising an aqueous phase as a depigmenting agent.

According to the invention, the term "hydrophilic active principle" is understood to mean a compound having a solubility in water of at least 0.25% at ambient temperature (25° C.).

According to the invention, the term "oxidation-sensitive hydrophilic active principle" is understood to mean any active principle of natural or synthetic origin capable of undergoing decomposition by an oxidation mechanism. This oxidation phenomenon can have several causes, in particular the presence of oxygen, of light or of metal ions, a high temperature or certain pH conditions.

Mention may be made, among ascorbic acid derivatives by way of example and without implied limitation, of: the salts or esters, in particular 5,6-di-O-dimethylsilylascorbate (sold by Exsymol under the reference PRO-AA), the potassium salt of dl-α-tocopheryl dl-ascorbyl phosphate (sold by Senju Pharmaceutical under the reference SEPIVITAL EPC), magnesium ascorbyl phosphate, sodium ascorbyl phosphate (sold by Roche under the reference Stay-C 50) and ascorbyl glucoside (sold by Hayashibara).

In a particularly advantageous aspect, the oxidation-sensitive hydrophilic active principle is ascorbic acid.

According to the invention, the term "maleic anhydride copolymer" is understood to mean any polymer obtained by copolymerization of one or more maleic anhydride comonomers and of one or more comonomers chosen from vinyl acetate, vinyl alcohol, vinylpyrrolidone, olefins comprising from 2 to 20 carbon atoms, such as octadecene, ethylene, isobutylene, diisobutylene or isooctylene, and styrene, the maleic anhydride comonomers optionally being partially or completely hydrolysed. Use will preferably be made of hydrophilic polymers, that is to say polymers having a solubility of water of greater than or equal to 2 g/l.

Copolymers which are more particularly suitable for the implementation of the invention are copolymers obtained by copolymerization of one or more maleic anhydride units of which the maleic anhydride units are in the hydrolysed form and preferably in the form of alkaline salts, for example in the form of ammonium, sodium, potassium or lithium salts.

In an advantageous aspect of the invention, the copolymer has a molar fraction of maleic anhydride units of between 0.1 and 1, more preferably between 0.4 and 0.9.

According to an advantageous aspect of the invention, the molar ratio of the maleic anhydride unit equivalent to the oxidation-sensitive hydrophilic active principle varies between 0.005 and 10 and preferably between 0.01 and 1.

The weight-average molar mass of the maleic anhydride copolymers will advantageously be between 1 000 and 500 000 and preferably between 1 000 and 50 000.

Use will preferably be made of a copolymer of styrene and of maleic anhydride in a 50/50 ratio.

Use may be made, for example, of the styrene/maleic anhydride (50/50) copolymer, in the form of an ammonium salt at 30% in water, sold under the reference SMA1000H® by Atofina or the styrene/maleic anhydride (50/50) copolymer, in the form of a sodium salt at 40% in water, sold under the reference SMA1000HNa® by Atofina.

The copolymer is present in the composition according to the invention in an amount sufficient to produce the desired effect, that is to say in an amount sufficient to stabilize the oxidation-sensitive hydrophilic active principle. Preferably, the copolymer is present at a concentration of between 0.1 and 40% by weight with respect to the total weight of the aqueous phase and more particularly at a concentration of between 0.1 and 10% by weight with respect to the total weight of the aqueous phase.

The compositions used according to the invention are intended for topical application to the skin and/or its superficial body growths and therefore comprise a physiologically acceptable medium, that is to say a medium compatible with cutaneous tissues, such as the skin, scalp, eyelashes, eyebrows, hair, nails and mucous membranes. This physiologically acceptable medium can more particularly be composed of water and optionally of a physiologically acceptable organic solvent chosen, for example, from lower alcohols comprising from 1 to 8 carbon atoms and in particular from 1 to 6 carbon atoms, such as ethanol, isopropanol, propanol or butanol; polyethylene glycols having from 6 to 80 ethylene oxide units; or polyols, such as propylene glycol, isoprene glycol, butylene glycol, glycerol or sorbitol.

When the physiologically acceptable medium is an aqueous medium, it generally has a pH which is compatible with the skin, preferably ranging from 3 to 9 and better still from 3.5 to 7.5.

The compositions according to the invention can be provided in any pharmaceutical dosage form used conventionally for topical application and in particular in the form of aqueous or aqueous/alcoholic solutions, of oil-in-water (O/W) or water-in-oil (W/O) or multiple (triple: W/O/W or O/W/O) emulsions, of aqueous gels or of dispersions of a fatty phase in an aqueous phase using spherules, it being possible for these spherules to be polymeric nanoparticles, such as nanospheres and nanocapsules, or lipid vesicles of ionic and/or nonionic type (liposomes, niosomes or oleosomes). These compositions are prepared according to the usual methods.

In addition, the compositions used according to the invention can be more or less fluid and can have the appearance of a white or coloured cream, of an ointment, of a milk, of a lotion, of a serum, of a paste or of a foam. They can optionally be applied to the skin in the form of an aerosol. They can also be provided in a solid form, for example in the form of a stick.

When the composition used according to the invention comprises an oily phase, the latter preferably comprises at least one oil. It can additionally comprise other fatty substances.

Mention may be made, as oils which can be used in the composition of the invention, of, for example:

hydrocarbonaceous oils of animal origin, such as perhydrosqualene;

hydrocarbonaceous oils of vegetable origin, such as liquid triglycerides of fatty acids comprising from 4 to 10 carbon atoms, such as triglycerides of heptanoic acid or octanoic acid, or alternatively, for example, sunflower, maize, soybean, gourd, grape seed, sesame, hazelnut, apricot, macadamia, arara, castor or avocado oils, triglycerides of caprylic/capric acids, such as those sold by Stéarineries Dubois or those sold under the names Miglyol 810, 812 and 818 by Dynamit Nobel, jojoba oil, or karite butter oil;

synthetic esters and ethers, in particular of fatty acids, such as the oils of formulae $R^1COOR^2$ and $R^1OR^2$ in which $R^1$ represents the residue of a fatty acid comprising from 8 to 29 carbon atoms and $R^2$ represents a branched or unbranched hydrocarbonaceous chain comprising from 3 to 30 carbon atoms, such as, for example, purcellin oil, isononyl isononanoate, isopropyl myristate, 2-ethylhexyl palmitate, 2-octyldodecyl stearate, 2-octyidodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as, pentaerythrityl tetraisostearate;

linear or branched hydrocarbons of mineral or synthetic origin, such as volatile or nonvolatile liquid paraffins and their derivatives, liquid petrolatum, polydecenes or hydrogenated polyisobutene, such as parleam oil;

fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol;

partially hydrocarbon-comprising and/or silicone-comprising fluorinated oils, such as those disclosed in the document JP-A-2-295912;

silicone oils, such as volatile or nonvolatile polymethylsiloxanes (PDMS) comprising a linear or cyclic silicone chain which are liquid or pasty at ambient temperature, in particular cyclopolydimethylsiloxanes (cyclomethicones), such as cyclohexasiloxane; polydimethylsiloxanes comprising pendent alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyltrimethyl-siloxydiphenylsiloxanes, diphenyl dimethicones, diphenylmethyidiphenyl-trisiloxanes, (2-phenylethyl) trimethylsiloxysilicates and polymethylphenylsiloxanes;

their mixtures.

The term "hydrocarbonaceous oil" is understood to mean, in the list of the oils mentioned above, any oil predominantly comprising carbon and hydrogen atoms and optionally ester, ether, fluorinated, carboxylic acid and/or alcohol groups.

The other fatty substances which can be present in the oily phase are, for example, fatty acids comprising from 8 to 30 carbon atoms, such as stearic acid, lauric acid, palmitic acid and oleic acid; waxes, such as lanolin, beeswax, carnauba or candelilla wax, paraffin or lignite waxes or microcrystalline waxes, ceresin or ozokerite, or synthetic waxes, such as polyethylene waxes or Fischer-Tropsch waxes; silicone resins, such as trifluoromethyl $C_{1-4}$ alkyl dimethicone and trifluoropropyl dimethicone; and silicone elastomers, such as the products sold under the names "KSG" by Shin-Etsu, under the names "Trefil", "BY29" or "EPSX" by Dow Corning or under the names "Gransil" by Grant Industries.

These fatty substances can be chosen in a way varied by a person skilled in the art in order to prepare a composition having the desired properties, for example of consistency or of texture.

According to a specific embodiment of the invention, the composition according to the invention is a water-in-oil (W/O) or oil-in-water (O/W) emulsion. The proportion of the oily phase in the emulsion can range from 5 to 80% by weight and preferably from 5 to 50% by weight with respect to the total weight of the composition.

The emulsions generally comprise at least one emulsifier chosen from amphoteric, anionic, cationic or nonionic emulsifiers, used alone or as a mixture, and optionally a coemulsifier. The emulsifiers are appropriately chosen according to the emulsion to be obtained (W/O or O/W). The emulsifier and the coemulsifier are generally present in the composition in a proportion ranging from 0.3 to 30% by weight and preferably from 0.5 to 20% by weight with respect to the total weight of the composition.

Mention may be made, for the W/O emulsions, for example, as emulsifiers, of dimethicone copolyols, such as the mixture of cyclomethicone and of dimethicone copolyol sold under the name "DC 5225 C" by Dow Corning, and alkyl dimethicone copolyols, such as the laurylmethicone copolyol sold under the name "Dow Corning 5200 Formulation Aid" by Dow Corning and the cetyl dimethicone copolyol sold under the name Abil EM 90$^R$ by Goldschmidt. Use may also be made, as surfactant of W/O emulsions, of a crosslinked solid organopolysiloxane elastomer comprising at least one oxyalkylenated group, such as those obtained according to the procedure of Examples 3, 4 and 8 of the document U.S. Pat. No. 5,412,004 and the examples of the document U.S. Pat. No. 5,811,487, in particular the product of Example 3 (synthetic example) of U.S. Pat. No. 5,412,004, and such as that sold under the reference KSG 21 by Shin Etsu.

Mention may be made, for the O/W emulsions, for example, as emulsifiers, of nonionic emulsifiers, such as esters of fatty acids and of glycerol which are oxyalkylenated (more particularly polyoxyethylenated); esters of fatty acids and of sorbitan which are oxyalkylenated; esters of fatty acids which are oxyalkylenated (oxyethylenated and/or oxypropylenated); ethers of fatty alcohols which are oxyethylenated (oxyethylenated and/or oxypropylenated); sugar esters, such as sucrose stearate; and their mixtures, such as the mixture of glyceryl stearate and of PEG-40 stearate.

In a known way, the cosmetic or dermatological composition of the invention can also comprise adjuvants conventional in the cosmetics or dermatological field, such as hydrophilic or lipophilic gelling agents, preservatives, solvents, fragrances, fillers, UV screening agents, bactericides, odour absorbers, colouring materials, plant extracts or salts. The amounts of these various adjuvants are those conventionally used in the field under consideration, for example from 0.01 to 20% of the total weight of the composition. These adjuvants, depending on their nature, can be introduced into the fatty phase, into the aqueous phase and/or into the lipid spherules.

Mention may be made, as fillers which can be used in the composition of the invention, for example, of pigments, silica powder; talc; particles of polyamide and in particular those sold under the name Orgasol by Atochem; polyethylene powders; microspheres based on acrylic copolymers, such as those made of ethylene glycol dimethacrylate/lauryl methacrylate copolymer which are sold by Dow Corning under the name Polytrap; expanded powders, such as hollow microspheres and in particular the microspheres sold under the name Expancel by Kemanord Plast or under the name Micropearl F 80 ED by Matsumoto; silicone resin microbeads, such as those sold under the name Tospearl by Toshiba Silicone; and their mixtures. These fillers can be present in amounts ranging from 0 to 20% by weight and preferably from 1 to 10% by weight with respect to the total weight of the composition.

According to a preferred embodiment, the compositions in accordance with the invention can additionally comprise at least one organic photoprotective agent and/or at least one inorganic photoprotective agent which is active in the UV-A and/or UV-B regions (absorbers), which are soluble in water or in fats or else are insoluble in the cosmetic solvents commonly used and which are chosen from the following agents, denoted below under their INCI names:

p-aminobenzoic acid (PABA) derivatives, in particular PABA, ethyl PABA, ethyl dihydroxypropyl PABA, ethylhexyl dimethyl PABA (sold in particular under the name "Escalol 507" by ISP), glyceryl PABA or PEG-25 PABA (sold under the name "Uvinul P25" by BASF), salicylic derivatives, in particular homosalate (sold under the name "Eusolex HMS" by Rona/EM Industries), ethylhexyl salicylate (sold under the name "Neo Heliopan OS" by Haarmann and Reimer), dipropylene glycol salicylate (sold under the name "Dipsal" by Scher), or TEA salicylate (sold under the name "Neo Heliopan TS" by Haarmann and Reimer), dibenzoylmethane derivatives, in particular butyl methoxydibenzoylmethane (sold in particular under the trade name "Parsol 1789" by Hoffmann-LaRoche), or isopropyl dibenzoylmethane, cinnamic derivatives, in particular ethylhexyl methoxycinnamate (sold in particular under the trade name "Parsol MCX" by Hoffmann-LaRoche), isopropyl methoxycinnamate, isoamyl methoxycinnamate (sold under the trade name "Neo Heliopan E 1000" by Haarmann and Reimer), cinoxate, DEA methoxycinnamate, diisopropyl methyl cinnamate, or glyceryl ethylhexanoate dimethoxycinnamate, ββ-diphenylacrylate derivatives, in particular octocrylene (sold in particular under the trade name "Uvinul N539" by BASF) or etocrylene (sold in particular under the trade name "Uvinul N35" by BASF), benzophenone, in particular benzophenone-1 (sold under the trade name "Uvinul 400" by BASF), benzophenone-2 (sold under the trade name "Uvinul D50" by BASF), benzophenone-3 or oxybenzone (sold under the trade name "Uvinul M40" by BASF), benzophenone-6 (sold under the trade name "Helisorb 11" by Norquay), benzophenone-8 (sold under the trade name "Spectra-Sorb UV-24" by American Cyanamid), benzophenone-12, or n-hexyl 2-(4-diethylamino-2-hydroxybenzoyl) benzoate, benzylidene camphor derivatives, in particular 3-benzylidene camphor (manufactured under the name "Mexoryl SD" by Chimex), 4-methylbenzylidene camphor (sold under the name "Eusolex 6300" by Merck) or polyacrylamidomethyl benzylidene camphor (manufactured under the name "Mesoryl SW" by Chimex), triazine derivatives, in particular anisotriazine (sold under the trade name "Tinosorb S" by Ciba Specialty Chemicals), ethylhexyl triazone (sold in particular under the trade name "Uvinul T150" by BASF), diethylhexyl butamido triazone (sold under the trade name "Uvasorb HEB" by Sigma 3V) or 2,4,6-tris(diisobutyl 4'-amino-benzalmalonate)-s-triazine, benzotriazole derivatives, in particular drometrizole trisiloxane (sold under the name "Silatrizole" by Rhodia Chimie) or methylene bisbenzotriazolyl tetramethylbutylphenol (sold in the solid form under the trade name "Mixxim BB/100" by Fairmount Chemical or in the micronized form in aqueous dispersion under the trade name "Tinosorb M" by Ciba Specialty Chemicals), anthranilic derivatives, in particular menthyl anthranilate (sold under the trade name "Neo Heliopan MA" by Haarmann and Reimer), imidazoline derivatives, in particular ethylhexyl dimethoxybenzylidene dioxoimidazoline propionate, benzalmalonate derivatives, in particular polyorganosiloxane comprising benzalmalonate functional groups (sold under the trade name "Parsol SLX" by Hoffmann-LaRoche), and their mixtures, inorganic photoprotective agents chosen from pigments or alternatively nanopigments (mean size of the primary particles: generally between 5 nm and 100 nm, preferably between 10 nm and 50 nm) formed from coated or uncoated metal oxides, such as, for example, titanium oxide (amorphous or crystalline in the rutile and/or anatase form), iron oxide, zinc oxide, zirconium oxide or cerium oxide nanopigments, which are all UV photoprotective agents well known per se; conventional coating agents, such as alumina and/or aluminium stearate; the nanopigments formed from coated or uncoated metal oxides are disclosed in particular in Patent Applications EP 518 772 and EP 518 773.

The organic photoprotective agents which are more particularly preferred are chosen from ethylhexyl salicylate, ethylhexyl methoxycinnamate, octocrylene, benzophenone-3, 4-methylbenzylidene camphor, 2,4,6-tris(diisobutyl 4'-amino-benzalmalonate)-s-triazine, anisotriazine, ethylhexyl triazone, diethylhexyl butamido triazone, methylene bis-benzotriazolyl tetramethylbutylphenol, drometrizole trisiloxane, and their mixtures.

The photoprotective agents are generally present in the compositions according to the invention in proportions ranging from 0.1 to 20% by weight with respect to the total weight of the composition and preferably ranging from 0.2 to 15% by weight with respect to the total weight of the composition.

In another advantageous aspect of the invention, the composition used can additionally comprise at least one other depigmenting or anti-pigmentation active principle.

The depigmenting or anti-pigmentation agents capable of being incorporated in the composition according to the present invention comprise, for example, the following compounds: kojic acid; ellagic acid; arbutin and its derivatives, such as those disclosed in Applications EP-895 779 and EP-524 109; hydroquinone; aminophenol derivatives, such as those disclosed in Applications WO 99/10318 and WO 99/32077, in particular N-cholesteryloxycarbonyl-para-aminophenol and N-ethyloxycarbonyl-para-aminophenol; iminophenol derivatives, in particular those disclosed in Application WO 99/22707; L-2-oxothiazolidine-4-carboxylic acid or procysteine, and its salts and esters; ascorbic acid and its derivatives, in particular ascorbyl glucoside and magnesium ascorbyl phosphate; 4-butylresorcinol or lucinol; thiourea and its derivatives; calcium D-pantetheinesulphonate; and plant extracts, in particular extracts of manzanita, of liquorice, of mulberry and of skullcap, without this list being limiting.

The composition according to the invention can be applied to the skin, hair, including body hair, eyelashes, nails or lips. It can thus be used in a cosmetic treatment process for depigmenting and/or lightening the skin and/or hair, including body hair, comprising the application of the composition according to the invention to the skin and/or hair, including body hair.

The examples which follow serve to illustrate the invention without, however, exhibiting a limiting nature. The compounds are, depending on the situation, cited according to chemical names or according to CTFA (International Cosmetic Ingredient Dictionary and Handbook) names.

EXAMPLES

Example 1

Accelerated Storage Test

The aim of this test is to study the decomposition of an oxidation-sensitive hydrophilic active principle after storing for two months at 45° C. Various solutions were prepared and their compositions are collated in the following table:

TABLE I

| Compositions in water | Ascorbic acid | Polymer 1 | Polymer 2 |
|---|---|---|---|
| Solution A Control | 15% | — | — |
| Solution B | 15% | 1% | — |
| Solution C | 15% | — | 1% |
| Solution D Control 2 | 5% | — | — |
| Solution E | 5% | 1% | — |
| Solution F | 5% | — | 1% |

All the solutions are brought to pH 6 with 8.9 mol/l KOH.

The percentages of the polymers are given as active material.

Polymer 1: Styrene/maleic anhydride (50/50) copolymer, in the form of an ammonium salt at 30% in water, sold under the reference SMA1000H® by Atofina.

Polymer 2: Styrene/maleic anhydride (50/50) copolymer, in the form of a sodium salt, sold under the reference SMA1000HNa® by Atofina.

The degree of decomposition measured is given by the ratio:

$$(C_0 - C_{2\ months})/C_0$$

with $C_0$ concentration of ascorbic acid at t=0 and $C_{2\ months}$ the concentration of ascorbic acid at t=2 months, under the conditions indicated in the above table. The concentration of ascorbic acid is determined by the HPLC technique (LaChrom Merck system). The analytical conditions are as follows:

Column: Lichrosphere100 RP18 (250 mm)

Eluent: 0.1M phosphate buffer, pH 2.1

Flow rate: 1 ml/min

Detection at 257 nm

Dilution of the sample such that the concentration of ascorbic acid is between 0.05 and 1 mg/ml.

The results obtained are collated in the following Table II:

TABLE II

| | Degree of decomposition after 2 months at 45° C. (in %) | |
|---|---|---|
| | under air, amber glass bottle | under nitrogen, aluminium flask |
| Solution A (Control 1) | 43 | 19.4 |
| Solution B | 16 | 13.8 |
| Solution C | 17.6 | 9.7 |

TABLE II-continued

| | Degree of decomposition after 2 months at 45° C. (in %) | |
|---|---|---|
| | under air, amber glass bottle | under nitrogen, aluminium flask |
| Solution D (Control 2) | 45.4 | 29.6 |
| Solution E | 13.4 | 4.1 |
| Solution F | 9 | 5.1 |

It is found, from Table II, that the stability of ascorbic acid, at a concentration of 5 or 15%, is improved in the presence of Polymer 1 and Polymer 2 of the invention, even in the presence of atmospheric oxygen, in comparison with the control.

As the polymers mentioned are hydrophilic, it will be sufficient to add them to an aqueous ascorbic acid solution to stabilize the ascorbic acid.

Example 2

Demonstration of the Activity With Regard to the Dendricity of Melanocytes

The aim of this test is to show the effect of the combination of ascorbic acid with a copolymer according to the invention on adjusting the melanogenesis of human keratinocyte-melanocyte cocultures.

Method: The cells are treated from inoculation with the ascorbic acid/styrene/maleic anhydride (50/50) copolymer, in the form of a sodium salt at 40% in water, combinations for 7 days.

Observations:

The melanocytes are labelled using the NK1beteb antibody (green colouring), which recognizes the melanosomes at every stage of maturation. The nuclei of all the cells, melanocytes and keratinocytes, are stained using propidium iodide (red colouring).

Results:
  In the absence of the ascorbic acid/styrene/maleic anhydride (50/50) copolymer, in the form of a sodium salt at 40% in water, combinations, the melanocytes in cocultures are highly dendritic. The pigment is visibly transferred to the neighbouring keratinocytes.
  In the presence of the ascorbic acid/styrene/maleic anhydride (50/50) copolymer, in the form of a sodium salt at 40% in water, combinations, the majority of the melanocytes show a reduced dendricity and some melanocytes become bipolar.
  For a higher concentration, the majority of the melanocytes are bipolar and the amount of pigment transferred to the keratinocytes is reduced.

Example 3

O/W Anti-Blemish Cream

The following composition is prepared in a way conventional to a person skilled in the art.

| $A_1$ - Sorbitan tristearate | 0.7 g |
|---|---|
| - Polyethylene glycol (40 EO) stearate | 1.6 g |

-continued

| | |
|---|---|
| - Cetyl alcohol | 3.2 g |
| - Glyceryl mono-, di-, tripalmitate/stearate | 2.4 g |
| - Myristyl myristate | 2 g |
| - Liquid fraction of karite butter | 2 g |
| - Preservative | 0.2 g |
| $A_2$ - Cyclopentadimethylsiloxane | 15 g |
| B - Demineralized water | 58.29 g |
| -Glycerol | 3 g |
| -Ascorbic acid | 5 g |
| -50% Potassium hydroxide | 2.97 g |
| - Styrene/maleic anhydride copolymer, ammonium salt at 30% in water (SMA1000H ®, Atofina) | 3.34 g |
| - Preservative | 0.2 g |
| C -Fragrance | 0.1 g |

This cream which is soft on application makes it possible to reduce pigmentary blemishes and confers good stability on ascorbic acid.

Example 4

Depigmenting Gel

The following composition is prepared in a way conventional to a person skilled in the art.

| | |
|---|---|
| - Demineralized water | 76.28 g |
| - Polyacrylamide/$C_{13}$-$C_{14}$ isoparaffin/Laureth-7 (Sepigel 305) | 2 g |
| - Silicone oil | 10 g |
| - Ascorbic acid | 5 g |
| - 50% Potassium hydroxide | 2.97 g |
| - Styrene/maleic anhydride copolymer, sodium salt at 40% in water (SMA1000HNa ®, Atofina) | 2.5 g |
| - Preservative | 0.25 g |
| - Sequestering agent | 0.1 g |

A fresh gel is obtained, which gel makes it possible to combat cutaneous blemishes and in which gel ascorbic acid has good stability.

All references, documents, applications, patents, publications, standards, tests, texts, etc., mentioned herein are specifically incorporated herein by reference.

The above description of the invention provides a full written description thereof, including the manner and process of making and using it, and enables one of ordinary skill in the art to make and use the invention as set forth above and in the following claims, all of which make up a part of the description. Further, one of ordinary skill is now able to both make and use the following embodiments which make up a part of the preferred embodiments of the invention:

A. Cosmetic use of a composition for lightening the skin and/or hair, including body hair, the said composition comprising at least one oxidation-sensitive hydrophilic active principle selected from the group consisting of ascorbic acid and its derivatives and at least one maleic anhydride copolymer, comprising one or more maleic anhydride comonomers and one or more comonomers selected from the group consisting of vinyl acetate, vinyl alcohol, vinylpyrrolidone, olefins comprising from 2 to 20 carbon atoms, and styrene, in a physiologically acceptable medium comprising an aqueous phase.

B. Use of a combination composed of at least one oxidation-sensitive hydrophilic active principle selected from the group consisting of ascorbic acid and its derivatives and of at least one maleic anhydride copolymer, comprising one or more maleic anhydride comonomers and one or more comonomers selected from the group consisting of vinyl acetate, vinyl alcohol, vinylpyrrolidone, olefins comprising from 2 to 20 carbon atoms, and styrene, in a cosmetic composition comprising an aqueous phase, as depigmenting agents.

C. Use of at least one oxidation-sensitive hydrophilic active principle selected from the group consisting of ascorbic acid and its derivatives and of at least one maleic anhydride copolymer, comprising one or more maleic anhydride comonomers and one or more comonomers selected from the group consisting of vinyl acetate, vinyl alcohol, vinylpyrrolidone, olefins comprising from 2 to 20 carbon atoms, and styrene, for the preparation of a dermatological composition comprising an aqueous phase which is intended to depigment the skin and/or hair, including body hair.

D. Use according to any one of embodiments A-C, wherein the hydrophilic active principle is selected from the group consisting of ascorbic acid derivatives, such as 5,6-di-O-dimethylsilylascorbate, the dl-α-tocopheryl dl-ascorbyl phosphate potassium salt, magnesium ascorbyl phosphate, sodium ascorbyl phosphate and ascorbyl glucoside.

E. Use according to any one of embodiments A-C, wherein the oxidation-sensitive hydrophilic active principle is ascorbic acid.

F. Use according to any one of embodiments A-E, wherein the maleic anhydride units of the copolymer are in the hydrolysed form and in the form of alkaline salts.

G. Use according to any one of embodiments A-F, wherein the oxidation-sensitive active principle and the copolymer are both in the aqueous phase.

H. Use according to any one of embodiments A-G, wherein the copolymer has a molar fraction of maleic anhydride units of between 0.1 and 1.

I. Use according to embodiment H, wherein the copolymer has a molar fraction of maleic anhydride units of between 0.4 and 0.9.

J. Use according to any one of embodiments A-I, wherein the copolymer is a copolymer of styrene and of maleic anhydride in a 50/50 ratio.

K. Use according to any one of embodiments A-J, wherein the copolymer is a copolymer of styrene and of maleic anhydride in a 50/50 ratio in the form of an ammonium or sodium salt.

L. Use according to any one of embodiments A-K, wherein the molar ratio of the maleic anhydride unit equivalent to the oxidation-sensitive hydrophilic active principle varies between 0.005 and 10.

M. Use according to embodiment L, wherein the molar ratio of the maleic anhydride unit equivalent to the oxidation-sensitive hydrophilic active principle varies between 0.01 and 1.

N. Use according to any one of embodiments A-M, wherein the copolymer is present at a concentration of between 0.1 and 40% by weight of the aqueous phase.

O. Use according to embodiment N, wherein the copolymer is present at a concentration of between 0.1 and 10% by weight of the aqueous phase.

P. Use according to any one of embodiments A-O, wherein the composition additionally comprises another depigmenting or antipigmentation agent.

Q. Use according to embodiment P, wherein the depigmenting or anti-pigmentation agent is selected from the group consisting of kojic acid; ellagic acid; arbutin and its derivatives; hydroquinone; aminophenol derivatives; iminophenol derivatives; L-2-oxothiazolidine-4-carboxylic acid or procysteine, and its salts and esters; 4-butylresorcinol or lucinol; thiourea and its derivatives; calcium D-pantetheinesulphonate; ascorbyl glucoside, magnesium ascorbyl phosphate; and plant extracts, in particular extracts of manzanita, of liquorice, of mulberry and of skullcap.

R. Cosmetic treatment process intended to depigment and/or lighten the skin and/or hair, including body hair, comprising the application, to the skin, and/or hair, including body hair, of a composition comprising at least one oxidation-sensitive hydrophilic active principle selected from the group consisting of ascorbic acid and its derivatives and at least one maleic anhydride copolymer, comprising one or more maleic anhydride comonomers and one or more comonomers selected from the group consisting of vinyl acetate, vinyl alcohol, vinylpyrrolidone, olefins comprising from 2 to 20 carbon atoms, and styrene.

S. A composition comprising at least one oxidation-sensitive hydrophilic active principle preferably selected from the group consisting of ascorbic acid and its derivatives and at least one maleic anhydride copolymer comprising one or more maleic anhydride comonomer units and one or more comonomer units selected from the group consisting of vinyl acetate, vinyl alcohol, vinylpyrrolidone, olefins comprising from 2 to 20 carbon atoms, and styrene, preferably further comprising a physiologically acceptable medium comprising an aqueous phase.

The invention claimed is:

1. A method for lightening and/or depigmenting the skin and/or hair comprising applying thereto a composition comprising at least one oxidation-sensitive hydrophilic active principle selected from the group consisting of ascorbic acid, 5,6-di-O-dimethylsilylascorbate, the dl-α-tocopheryl dl-ascorbyl phosphate potassium salt, magnesium ascorbyl phosphate, sodium ascorbyl phosphate, ascorbyl glucoside, and mixtures thereof, and at least one water-soluble maleic anhydride copolymer comprising one or more hydrolyzed maleic anhydride comonomer units and one or more comonomer units selected from the group consisting of vinyl acetate, vinyl alcohol, vinylpyrrolidone, olefins comprising from 2 to 20 carbon atoms, and styrene, said composition further comprising a physiologically acceptable medium comprising an aqueous phase, wherein the oxidation-sensitive active principle and the copolymer are in the same aqueous phase.

2. The method according to claim 1, wherein the hydrophilic active principle is selected from the group consisting of 5,6-di-O-dimethylsilylascorbate, the dl-α-tocopheryl dl-ascorbyl phosphate potassium salt, magnesium ascorbyl phosphate, sodium ascorbyl phosphate and ascorbyl glucoside.

3. The method according to claim 1, wherein the oxidation-sensitive hydrophilic active principle is ascorbic acid.

4. The method according to claim 1, wherein the hydrolyzed maleic anhydride units of the copolymer are in the form of alkaline salts.

5. The method according to claim 1, wherein the copolymer has a molar fraction of maleic anhydride units of between 0.1 and 0.9.

6. The method according to claim 1, wherein the copolymer has a molar fraction of maleic anhydride units of between 0.4 and 0.9.

7. The method according to claim 1, wherein the copolymer is a copolymer of styrene and of maleic anhydride in a 50/50 ratio.

8. The method according to claim 1, wherein the copolymer is a copolymer of styrene and of maleic anhydride in a 50/50 ratio in the form of an ammonium or sodium salt.

9. The method according to claim 1, wherein the molar ratio of the maleic anhydride unit equivalent to the oxidation-sensitive hydrophilic active principle is between 0.005 and 10.

10. The method according to claim 9, wherein the molar ratio of the maleic anhydride unit equivalent to the oxidation-sensitive hydrophilic active principle is between 0.01 and 1.

11. The method according to claim 1, wherein the copolymer is present at a concentration of between 0.1 and 40% by weight of the aqueous phase.

12. The method according to claim 11, wherein the copolymer is present at a concentration of between 0.1 and 10% by weight of the aqueous phase.

13. The method according to claim 1, wherein the composition further comprises at least one depigmenting or antipigmentation agent in addition to the active principle.

14. The method according to claim 13, wherein the depigmenting or antipigmentation agent is selected from the group consisting of kojic acid; ellagic acid; arbutin and its derivatives; hydroquinone; aminophenol derivatives; iminophenol derivatives; L-2-oxothiazolidine-4-carboxylic acid or procysteine, and its salts and esters; 4-butylresorcinol or lucinol; thiourea and its derivatives; calcium D-pantetheinesulphonate; ascorbyl glucoside, magnesium ascorbyl phosphate; and plant extracts.

15. A composition comprising at least one oxidation-sensitive hydrophilic active principle selected from the group consisting of ascorbic acid, 5,6-di-O-dimethylsilylascorbate, the dl-α-tocopheryl dl-ascorbyl phosphate potassium salt, magnesium ascorbyl phosphate, sodium ascorbyl phosphate, ascorbyl glucoside, and mixtures thereof and at least one hydrolyzed maleic anhydride copolymer comprising one or more maleic anhydride comonomer units and one or more comonomer units selected from the group consisting of vinyl acetate, vinyl alcohol, vinylpyrrolidone, olefins comprising from 2 to 20 carbon atoms, and styrene, wherein the oxidation-sensitive active principle and the copolymer are both in the aqueous phase.

16. The composition according to claim 15, said composition further comprising a physiologically acceptable medium comprising an aqueous phase.

17. The method according to claim 1, comprising lightening the skin by applying thereto a composition comprising at least one oxidation-sensitive hydrophilic active principle selected from the group consisting of ascorbic acid, 5,6-di-O-dimethylsilylascorbate, the dl-α-tocopheryl di-ascorbyl phosphate potassium salt, magnesium ascorbyl phosphate, sodium ascorbyl phosphate, ascorbyl glucoside, and mixtures thereof, and at least one maleic anhydride copolymer comprising one or more hydrolyzed maleic anhydride comonomer units and one or more comonomer units selected from the group consisting of vinyl acetate, vinyl alcohol, vinylpyrrolidone, olefins comprising from 2 to 20 carbon atoms, and styrene, said composition further comprising a physiologically acceptable medium comprising an aqueous phase, in an amount sufficient to lighten the skin.

18. The method according to claim 1, comprising depigmenting the skin by applying thereto a composition comprising at least one oxidation-sensitive hydrophilic active principle selected from the group consisting of ascorbic acid, 5,6-di-O-dimethylsilylascorbate, the dl-α-tocopheryl dl-ascorbyl phosphate potassium salt, magnesium ascorbyl phosphate, sodium ascorbyl phosphate, ascorbyl glucoside, and mixtures thereof, and at least one maleic anhydride copolymer comprising one or more hydrolyzed maleic anhydride comonomer units and one or more comonomer units selected from the group consisting of vinyl acetate, vinyl alcohol, vinylpyrrolidone, olefins comprising from 2 to 20 carbon atoms, and styrene, said composition further comprising a physiologically acceptable medium comprising an aqueous phase, in an amount sufficient to depigment the skin.

19. The method according to claim 1, wherein the copolymer consists of maleic anhydride and styrene units.

* * * * *